United States Patent [19]

Havstad et al.

[11] 4,237,906
[45] Dec. 9, 1980

[54] ANTIGEN INJECTION ASSEMBLY

[76] Inventors: Harold R. Havstad, 3344 Rogue River Dr., Eagle Point, Oreg. 97524; Isadore Pitesky, 4001 Linden Ave., Long Beach, Calif. 90806

[21] Appl. No.: 966,854

[22] Filed: Dec. 6, 1978

[51] Int. Cl.³ .............................................. A61B 5/10
[52] U.S. Cl. ................................... 128/743; 128/253; 128/333; 215/250
[58] Field of Search ...................... 128/743, 333, 253; 215/250, 355, DIG. 1, DIG. 3

[56] References Cited

U.S. PATENT DOCUMENTS

| 66,212 | 7/1867 | Burnet | 215/250 |
|---|---|---|---|
| D. 247,822 | 5/1978 | Hein et al. | 128/743 X |
| 841,896 | 1/1907 | Richardson | 215/250 |
| 3,074,580 | 1/1963 | Golde | 215/250 |
| 3,221,739 | 12/1965 | Rosenthal | 128/253 |
| 3,221,740 | 12/1965 | Rosenthal | 128/253 |
| 3,246,647 | 4/1966 | Taylor et al. | 128/253 |
| 3,512,520 | 5/1970 | Cowan | 128/743 |

FOREIGN PATENT DOCUMENTS

| 1132208 | 3/1957 | France | 215/250 |
|---|---|---|---|
| 438065 | 11/1967 | Switzerland | 215/250 |

*Primary Examiner*—Kyle L. Howell
*Attorney, Agent, or Firm*—William C. Babcock

[57] ABSTRACT

A tray having a number of spaced, individually spaced cavities extending downwardly therein in which tubular containers are removably disposed that contain biological active liquids. The containers have open tops in which resilient stoppers are sealingly disposed. Each stopper has a longitudinal bore therein that terminates on the upper end in a projecting bubble. Each bubble may be severed from the stopper with which it is associated by cutting transversely through the base of the bubble with a sharp sterile instrument such as a razor blade or the like. Immediately upon the bubble being severed, an elongate sterile applicator is removably and sealingly disposed in the bore associated with that bubble The applicator includes a handle from which a tapered shank projects to terminate in a flat first end from which a number of spaced needle like projections extend, with the projections being of a length that is the depth that is desired to have same penetrate into the skin. When the applicator is slidably removed from the bore in a stopper, a predetermined quantity of the biological active liquid will adhere. When the projections are forced into the skin of a patient the adhering liquid is transferred to the patient. The first end of the shank acts as a stop by contact with the skin of the patient. The applicator assures not only that a predetermined amount of liquid will be injected into a patient, but limits the depth to which such injection will be made. The applicator after use is discarded, and a new sterile applicator is inserted in the bore of a stopper to seal the liquid in the container associated with that stopper from contact with the ambient atmosphere.

1 Claim, 8 Drawing Figures

U.S. Patent     Dec. 9, 1980     4,237,906
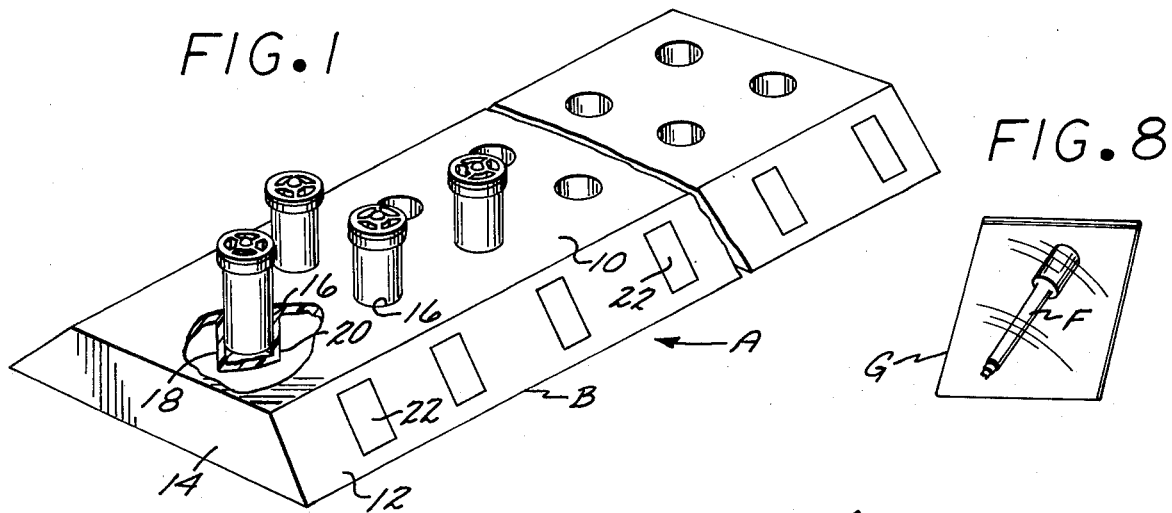
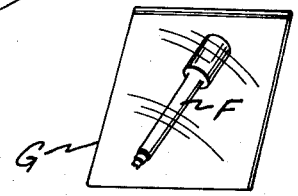
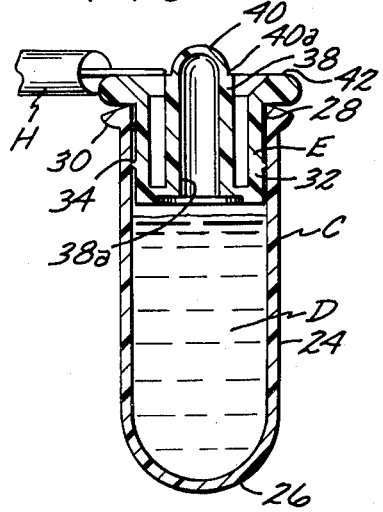

ANTIGEN INJECTION ASSEMBLY

BACKGROUND OF THE INVENTION

1. Field of the Invention
Injection Assembly.

2. Description of the Prior Art

In the proper testing for allergies it is necessary that predetermined quantities of antigens be injected to predetermined depths below the skin of a patient for the physician to note the reaction to such injections.

Although numerous devices have been devised and used in the past for making such injections, none of the prior art devices maintain the biological active liquids in hermetically sealed containers that are removably arranged in an identified relationship on a portable tray and include applicators that assure that a nurse will inject but a predetermined quantity of an antigen or other biological active liquid to a predetermined depth below the skin of a user.

A major object of the present assembly is to overcome the operational disadvantages of prior art injection devices by providing a portable assembly of hermetically sealed containers for biological liquids that have applicators removably associated therewith that assure but a predetermined quantity of biological active liquid will be injected under the skin of a patient and to a predetermined depth.

Another object of the invention is to provide an assembly that is simple and easy to use, may be fabricated from standard commercially available material, and one that permits the efficient injection of predetermined quantities of biological active liquids to predetermined depths under the skin of a patient by nurses and personnel that have but limited experience and skill in making such injections.

SUMMARY OF THE INVENTION

A number of open top sterile containers are provided each of which holds a quantity of a liquid biological active substance such as an antigen or the like. A resilient stopper is provided for each container, which stopper when positioned in the open top portion thereof hermetically seals the liquid in the container from contact with the ambient atmosphere. Each stopper includes a centrally disposed upwardly extending bubble of substantial diameter.

A tray is provided that includes a top that has a number of spaced downwardly extending recessed portions. Each of the recessed portions is of such diameter as to snugly and removably support one of the containers. Labels are secured to the tray to identify the biological active liquids in the containers.

A number of sterile applicators are provided, each of which is enclosed within a sterile envelope. Each applicator includes a handle from which a tapered stem projects that terminates in a flat free end. A number of spaced needle-like projections extend outwardly from the flat free end of the tapered stem. The length of each projection is the same as the depth to which it is desired to inject a biological liquid below the skin of a patient.

Prior to the invention being used a sterile razor blade or other sharp knife-like instrument is used to sequentially transversely sever the bubbles, to provide downwardly extending openings in the stoppers. The diameter of each opening so formed is less than that of the first free end of a stem, and the portion of the stem adjacent the handle being of greater diameter than the opening.

Thus, when an applicator is removed from a sterile envelope, and the stem thereof slidably inserted in an opening, a surface portion of the tapered stem intermediate the free end and the handle will pressure seal with the edge portion of the stopper defining the opening.

When it is desired to inject a particular biological active liquid into a patient, the appropriate applicator will be removed from the container, with a film of the liquid adhering to the projections and the free end. By use of the handle of the applicator, the projections are forced to penetrate the skin, with the biological liquid that adhered to the projections being transferred to the flesh of the patient below the skin. Each application is uniform, for only a specific quantity of the biological active liquid will adhere to the projections, and the projections being limited as to the depth of penetration due to the flat free end contacting the skin and acting as a stop.

After the injection has been completed, the applicator that was used is discarded, and a new applicator is removed from its protective envelope. The new applicator is inserted immediately in the opening in the stopper that was previously occupied by the discarded applicator.

BRIEF DESCRIPTION OF THE DRAWINGS

FIG. 1 is a perspective view of a tray having spaced recessed portions in which containers holding biologically active liquids may be removably disposed;

FIG. 2 is a longitudinal cross-sectional view of one of the containers having a stopper mounted therein, which stopper includes an upwardly projecting bubble;

FIG. 3 is the same view as shown in FIG. 2 but after the bubble has been severed by a sharp instrument such as a razor blade or the like;

FIG. 4 is a longitudinal cross-sectional view of the container and stopper, with an applicator sealingly and removably mounted in a bore that extends through the stopper;

FIG. 5 is an enlarged perspective view of the free end of the applicator stamp illustrating a number of projections that extend therefrom and which penetrate the skin of a user to inject biological active liquid thereunder, with the depth that the projections penetrate the skin being limited by the flat free end of the stem which acts as a stop when in contact with the skin of the patient;

FIG. 6 is a fragmentary side elevational view of the lower portion of the stem illustrating the projections that extend therefrom in spaced relationship;

FIG. 7 is a fragmentary longitudinal cross-sectional view of the stem and illustrating the manner in which the projections penetrate the skin and the lower end of the stem acting as a stop to limit the depth of such penetration; and FIG. 8 is a perspective view of one of the applicators enclosed in a sterile envelope prior to the applicator being used.

DESCRIPTION OF THE PREFERRED EMBODIMENT

The invention A as may best be seen in FIG. 1 includes a tray B that is preferably molded from a commercially available polymerized resin. The tray B includes a flat top 10, a pair of side walls 12 that taper downwardly and outwardly therefrom, and a pair of similarly tapered end walls 14. The top 10 has a number of spaced openings 16 defined therein, with cups 18 extending downwardly from the openings and preferably molded as an integral part of the top 10. Each of the cups 18 defines a downwardly extending recess 20.

A number of containers C are provided, each of which holds a quantity of a biologically active liquid, such as an antigen or the like. The containers C may be made from a suitable plastic material, glass or the like, and are preferably transparent to permit the quantity of the biological active liquid D to be visualized therein. Each of the containers C includes a cylindrical side wall 24, as may best be seen in FIGS. 2–4 inclusive, which side wall terminates in a semi-spherical bottom 26. Each container C has an upper open end 28, and a circumferentially extending bead 30 that projects outwardly from the upper extremity of the side wall 24.

A number of stoppers E are provided, each of which is formed from a resilient material such as plastic or the like. Each stopper E includes a cylindrical side wall 32 that has a number of circumferentially extending, longitudinally spaced sealing ribs 34 projecting therefrom. The side wall 32 terminates on the lower end in a transverse ring-shaped web 36, which web has a tube 38 extending upwardly from the inner periphery thereof. Each tube terminates on the upper end in a semi-circle bubble 40, with the base 40a of the bubble being flush with the upper surface 42 of the side wall 32.

A number of applicators F are provided, each of which is disposed within the interior of a sealed sterile transverse envelope G and is shown in FIG. 8. Each applicator F includes a cylindrical handle 44 that has an elongate stem 46 projecting from one end thereof, with the stem having a downwardly and inwardly tapering side wall 48 as may be seen in FIG. 4. The stem 46 on the lower end thereof develops into a cylindrical portion 50 of reduced diameter, and the portion 50 terminating in a first transverse end 52. A number of circumferentially spaced pointed projections 54 extend from the flat ends 52. When the applicator is moved into pressure contact with the skin 56 of a patient (not shown) the projection 54 penetrates the skin and extends into the flesh 58 of the patient.

When the stoppers E are removably disposed in the upper portion of one of the containers C, the sealing ribs 34 are in pressure sealing engagement with the interior of the side wall 32, and the sealing ribs in cooperation with the bubble 40 preventing entry of foreign material from the ambient atmosphere into the interior of the containers C to contaminate the biological active liquid D therein. The containers C when in this condition are placed in the tray B as shown in FIG. 1, with the identity of the biological active liquid in each container being indicated on one of the labels 22 most adjacent the container. Prior to the invention A being used, a sharp instrument H such as a razor or a knife is used to sever the bubbles 40 from the stopper E at the base 40a of the bubble as illustrated in FIG. 2. After a bubble 40 has been so severed, an applicator F is removed from the envelope G and the stem 46 thereof slid downwardly in the bore 38a as shown in FIG. 4, and the tapered surface 48 of the stem pressure contacting the interior surface 38a of the tube 38 to seal therewith, and prevent contaminants from the atmosphere moving downwardly through the tube 38.

The invention A is used as follows.

The containers C are sterilized and then partially filled with a biological active liquid D as shown in FIGS. 2 and 3. Sterile stoppers E are then inserted in the upper open ends of the containers. The containers C as so filled and stopped are placed in the tray B as shown in FIG. 1, with the identity of the biological active liquid being indicated on a label secured to the tray adjacent the cup 18 in which the container C is disposed.

When it is desired to start using a particular biological active liquid D, the bubble 40 is severed from the stopper E with a sharp instrument H such as a sterile knife, razor blade or the like. When the bubble 40 is so severed an entrance is provided into the bore 38a of tube 38.

A number of applicators F are provided each of which is encased in a sterile envelope G. After a bubble 40 has been severed, an applicator F is taken immediately from an envelope G and extended longitudinally downward into a bore 38a. The stem 46 due to the tapered external surface thereof removably seals with the surface 38a of bore 38. The stem 46 is formed of a polymerized resin that will be wet by the biological active liquid D, with a film of the liquid adhering to the projections 54. The liquid adhering to the stem surface 48 will be substantially wiped therefrom by contact with tube 38 as the stem is withdrawn through bore 38a and will flow back into container C.

When the applicator F is moved into pressure contact with the skin 56 of a patient, the projections 54 will penetrate the same and transfer the film of biological active liquid D adhering thereto to the flesh 58 underlying the skin. The depth the projections 54 can penetrate the skin is limited due to the flat end surface contacting the skin 56 and acting as a stop. After an applicator F has been used for an injection it is discarded, and a fresh sterile applicator is inserted in the bore 38a from which the discarded applicator was removed.

The applicators F not only serve in cooperation with stoppers E to seal the biological active liquid D in a container C from contact with the ambient atmosphere, but also serve to inject a predetermined quantity of the liquid to a desired depth under the skin of a patient.

The liquid D has been referred to generally as biological active and may be one that contains allergens or other materials which when injected give a reaction or produce a desired result for the physician.

The use and operation of the invention has been described previously in detail and need not be repeated.

What is claimed is:

1. A portable assembly for removably storing a plurality of different biological active antigen liquids in sealed test tube shaped containers that are removably maintained in spaced relationship with one another both in storage and when in used, with the contents of each of said containers being visually identified both when said containers are in storage and when in use, and said containers in cooperation with applicators permitting said antigen liquids to be intermittently dispensed from said containers and injected under the skin of a plurality of patients to a desired depth, said assembly including:

a. a tray that includes a flat generally rectangular top that has a plurality of longitudinally spaced and transversely aligned openings therein, a plurality of walls that extend downwardly and outwardly from the sides and ends of said top and that may rest on a horizontal surface, a plurality of cups that extend downwardly from said openings in said top a distance less than the height of a plurality of antigen containers removably supported by said cups said walls, said cups of a length substantially less than that of said containers, with substantial portions of said containers extending upwardly above said top to permit said containers to be grasped and removed from said tray when the occasion so requires, and visual means on said tray that indicate the identity of said antigen liquids in said containers disposed in said transverse openings and cups;

b. a plurality of stoppers formed from an inert plastic material that sealingly engage the interior surfaces of said containers adjacent the open tops thereof to sealingly maintain said antigen liquids thereof out of contact with the ambient atmosphere except when said antigen liquids are being dispensed, each of said stoppers including:

1. a cylindrical side wall that has an upper open end and a lower end, a plurality of longitudinally spaced, circumferentially extending sealing rings that extend outwardly from said side wall and pressure seal with the interior surface of said cup, and a circumferentially extending lip that extends outwardly from said upper end of said side wall;
2. a ring-shaped web that extends inwardly from said lower end of said side wall;
3. a tube that extends upwardly longitudinally from the inner periphery of said web within said side wall, said tube including a bubble on the upper end thereof that projects above said lip, said bubble when severed from said tube in a plane common with the upper extremity of said lip providing said entrance into a bore in said tube;

c. a plurality of applicators that are each formed as an integral unit from a polymerized resin that will be wet by one of said antigen liquids, each of said applicators including a handle that has a stem projecting therefrom that has a tapered external surface, said external surface adjacent said handle having a diameter greater than that of said entrance, said stem terminating in a flat free end of smaller diameter than that of said entrance, and a plurality of spaced sharp projections that extend outwardly from said free end, said applicator capable of being moved downwardly longitudinally in said bore in one of said stoppers until a portion of said tapered surface intermediate said free end and said handle pressure seals with a portion of said stopper defining said bore, said applicator each time it is sequentially removed from said stopper having a film of said biological active liquid in uniform volume adhering to said projections which when said projections are forced through the skin of a patient by pressure contact therewith is transferred to the flesh underlying said skin, and the depth of penetration of said projections being limited by said free end contacting the skin of the patient and acting as a stop to further penetration, with the applicator after such injection being discarded, and a sterile one of said applicators now inserted in said stopper for use in making a future injection and cooperating with said stopper to seal said container until said future injection is made; and d. means for maintaining said applicators in a sterile condition until just prior to each said applicators being inserted in one said stoppers for subsequent use in dispensing an injection of said antigen liquid under the skin of a patient.

* * * * *